United States Patent
Distler et al.

(10) Patent No.: US 9,888,886 B2
(45) Date of Patent: Feb. 13, 2018

(54) ROTOR WITH A BACKPLANE BUS HAVING ELECTRICAL CONNECTION ELEMENTS TO MAKE ELECTRICAL CONTACT WITH ELECTRICAL COMPONENTS IN A MEDICAL APPARATUS, AS WELL AS ROTATING UNIT AND MEDICAL APPARATUS WITH SUCH A ROTOR

(71) Applicant: Siemens Aktiengesellschaft, Munich (DE)

(72) Inventors: Friedrich Distler, Fuerth (DE); Sultan Haider, Erlangen (DE); Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 404 days.

(21) Appl. No.: 14/516,911

(22) Filed: Oct. 17, 2014

(65) Prior Publication Data
US 2015/0110253 A1 Apr. 23, 2015

(30) Foreign Application Priority Data
Oct. 18, 2013 (DE) .................. 10 2013 221 169

(51) Int. Cl.
*A61B 6/00* (2006.01)
*A61B 6/03* (2006.01)
*H01R 39/10* (2006.01)
*H05K 1/00* (2006.01)

(52) U.S. Cl.
CPC ............ *A61B 6/035* (2013.01); *A61B 6/4476* (2013.01); *A61B 6/56* (2013.01); *H01R 39/10* (2013.01); *H05K 1/00* (2013.01); *A61B 6/4447* (2013.01); *H01R 2201/12* (2013.01)

(58) Field of Classification Search
CPC .................................. A61B 6/035; A61B 6/56
See application file for complete search history.

(56) References Cited

U.S. PATENT DOCUMENTS

| 6,337,894 | B1 | 1/2002 | Tybinkowski et al. |
| 2003/0062482 | A1* | 4/2003 | Williams ............... G01T 1/17 250/363.03 |
| 2004/0022350 | A1* | 2/2004 | Gregerson ............. A61B 6/032 378/15 |
| 2004/0260176 | A1 | 12/2004 | Wollenweber et al. |
| 2007/0165770 | A1* | 7/2007 | Vogtmeier ............ G01T 1/2985 378/4 |
| 2007/0230654 | A1 | 10/2007 | Chappo et al. |
| 2010/0025591 | A1 | 2/2010 | Luecke et al. |

(Continued)

FOREIGN PATENT DOCUMENTS

| CN | 1419893 A | 5/2003 |
| CN | 101685072 A | 3/2010 |

(Continued)

*Primary Examiner* — Dani Fox
(74) *Attorney, Agent, or Firm* — Schiff Hardin LLP

(57) ABSTRACT

A rotor of a computed tomography apparatus has a rotatable mechanical support frame for mechanical retention of electrical components and electrical connection elements for electrical connection with electrical components of the computed tomography apparatus, with the electrical connection elements arranged in at least one backplane bus. A rotating unit and a computed tomography apparatus embody such a rotor.

15 Claims, 3 Drawing Sheets

(56) References Cited

U.S. PATENT DOCUMENTS

| | | | |
|---|---|---|---|
| 2010/0303209 A1 | 12/2010 | Luhta et al. | |
| 2011/0142304 A1 | 6/2011 | Stearns | |
| 2012/0256099 A1* | 10/2012 | Gregerson | A61B 6/035 250/453.11 |

FOREIGN PATENT DOCUMENTS

| | | |
|---|---|---|
| CN | 102508456 A | 6/2012 |
| CN | 103330571 A | 10/2013 |
| DE | 102004057002 A1 | 6/2006 |
| EP | 0125879 A1 | 5/1984 |

\* cited by examiner

ROTOR WITH A BACKPLANE BUS HAVING ELECTRICAL CONNECTION ELEMENTS TO MAKE ELECTRICAL CONTACT WITH ELECTRICAL COMPONENTS IN A MEDICAL APPARATUS, AS WELL AS ROTATING UNIT AND MEDICAL APPARATUS WITH SUCH A ROTOR

BACKGROUND OF THE INVENTION

Field of the Invention

The invention concerns a rotor of a computed tomography (CT) apparatus with a rotatable mechanical support frame for mechanical retention of electrical components and electrical connection elements for electrical connection with electrical components of the computed tomography apparatus, wherein the electrical connection elements are arranged in at least one backplane bus. Furthermore, the invention concerns a rotating unit and a computed tomography apparatus with such a rotor.

Description of the Prior Art

Computed tomography apparatuses are used often for medical imaging,—a primary field of apparatus of the present invention. A computed tomography apparatus essentially has a stationary part and a rotating or rotatable part, and the rotatable part has an acquisition system that includes at least one radiation source and one detector attached to a frame that is mounted such that it can rotate. Such a rotatable frame or rotor has a continuous opening therein for passage of a patient or an examination subject through the rotor, and typically has a stationary support frame and a rotatable support frame for attachment (bolting, for example) of the electrical components of the rotor, in particular of the acquisition system.

In the use of such apparatuses, a very large amount of measurement data must be acquired in a very short time, and must be transmitted to an image reconstruction unit so as to be processed further to reconstruct the desired images. It is furthermore known that, in computed tomography with CT systems having a continuously rotating part, both electrical power and electrical signals must be transmitted between the stationary part and the rotating part of the computed tomography apparatus, and between the different components of the rotating part. Like the x-ray tube and the x-ray detector, the components arranged on the rotatable part, or rotor of the computed tomography apparatus, need an electrical power supply. Large amounts of electrical power are normally transmitted with the use of slip contacts, while electrical signals, as used in data transfer of detector data or time signals and/or control signals, are normally transmitted with the use of no-contact data transfer, for example capacitively or optically. An immense power transfer and an intensive data exchange occur between the stationary part and the rotating part of the gantry of a CT apparatus.

Current computed tomography apparatuses typically have multiple slip rings, in particular for power transmission from the stationary part to the rotating part of the computed tomography apparatus, wherein at least one of the power transmission paths is provided for the radiation source. Numerous electrical connections with cable lines and plug-in elements that are partially attached are already realized at such slip rings. In addition, the different electrical components of the rotor (for example the detector or the radiation source) of such a computed tomography apparatus are typically mounted on (screwed on, for example) the rotating part of the apparatus, wherein the different components are connected among one another or to the respective power supply connections and data connections with conductors (with cables, for example). The cables or the conductors are attached to the rotating part with the use of cable mounts or cable retainers such that the conductors or the cable connections are stable even under the effect of the centrifugal force in the rotating state. For this purpose, among other things the realization of additional anchor points on the rotating part is necessary. For example, additional attachment points are realized by special arrangements of metal layers with special receptacles for the cable retainers, these arrangements being bolted onto the rotating part.

Furthermore, the power transmission—and in general also the signal transmission—between the different components on the rotating part of the computed tomography apparatus is likewise realized in part by plug connections between the respective cables and components. However, in rotating systems this type of connection is only conditionally advantageous due to the centrifugal forces acting on the components and the partial mobility of the cables. At high velocities or given velocity changes, the stability and the longevity of such electrical connections are problematical, particularly given the transmission of large amounts of electrical power. The connections thus must be checked or repaired regularly. Moreover, the cable connections consume a large amount of material (in particular copper), so the total costs are increased. Given each additional component to be attached to the rotating part, the number of cables, the material costs and the weight of the apparatus thus increase. The integration of new components on the rotating part is also complicated due to the cables and cable anchoring devices that are already present. Lastly, the cable connections must be individually mounted and attached, which is complicated. In the event of service, for example for the exchange of a component, first these must be individually demounted and attached again, which increases the work time.

SUMMARY OF THE INVENTION

An object of the invention is to provide a medical imaging apparatus, in particular a computed tomography apparatus, in which the electrical contacting of the electrical components is simplified. A robust power and signal transmission should also be achieved between the stationary part of the medical imaging apparatus and the components of the rotating part, as well as between the components of the rotating part among one another, such that the power transmission or the signal transmission within the rotor and from the rotor to the stationary part of the computed tomography apparatus is of simple design, and both the installation and the deinstallation or the exchange of electrical components of the rotor is simplified.

The invention is based on replacing all (or at least most) cables and plug elements that are typically used on the rotor for electrical contacting of the electrical components of the rotor, with at least one common backplane bus. The individual electrical components are modified such that both a mechanical connection and at least one electrical connection are created via their attachment to the rotor. The electrical connection thereby in particular enables at least a power transmission or signal transmission.

According to the present invention, a rotor has a rotatable mechanical support frame for mechanical mounting or attachment of electrical components, at least one backplane bus, and electrical connection elements for electrical connection with the electrical components, wherein the electrical connection elements are arranged in the at least one backplane bus. At the rotor, at least a portion of the electrical contacting of the electrical components of the rotor—preferably the electrical contacting of the electrical components among one another and/or the electrical contacting of the electrical components with external components—can be realized directly, or at least without loose cables. Cables and plug elements (and thus material) thus can thereby be avoided.

The components of the rotatable part preferably have connectors that are designed such that they can be connected directly (or at least without loose cables) with the electrical connection elements. For example, such connectors can be designed as plug socket arrangements or plug arrangements. The electrical components designed in this manner can be connected simply with the electrical connection elements. Electrical connection elements in particular include electrical feed lines. Such electrical feed lines are preferably designed to transmit signals and/or power. These electrical connection elements are preferably connectable at least on one side with at least one electrical component of the rotatable part of a medical imaging apparatus, or preferably form at least one electrical connection between at least two components of the rotatable part of a medical imaging apparatus. The electrical connection elements preferably form multiple electrical connections between at least two components of the rotatable part of a medical imaging apparatus. These electrical connection elements are preferably integrated into the backplane bus. The installation, deinstallation and/or exchange of the individual electrical components are thereby simplified. The necessity of providing additional anchoring points for the mechanical attachment of the cables to the rotor is thereby also done away with, whereby both space and weight and material are saved.

In an embodiment of the rotor according to the invention, the electrical connection elements are designed for signal and/or power transmission. For example, both image data and (for example) control data are encompassed as such a signal. The planning of the electrical contacting of the electrical components can take place separately from mechanical considerations for the attachment of the components.

In another embodiment of the rotor, the rotor has at least two backplane buses. Electrical connection elements for signal transmission are preferably arranged in a first backplane bus while electrical connection elements for power transmission are preferably arranged in a second backplane bus. The first backplane bus is preferably designed primarily for image data transmission and/or control data transmission. Additional backplane buses can also be provided for image data transmission, control data transmission or transmission of other electrical signals. A physical separation of the different transmissions is thereby achieved, which enables a targeted production of the corresponding electrical connection elements differently and independently of one another on the respective backplane bus. Different criteria and different qualities can thus be chosen for the different backplane buses, or for the different conductors and/or connectors depending on the transmission path, and depending on the provided function. The production of the individual backplane buses is thereby simplified, and at the same time a function separation is enabled. One backplane bus is advantageously mounted laterally to an additional backplane bus, preferably attached thereto. Alternatively, at least two backplane buses form a unit, or are designed so as to be integrated with one another or as one piece.

Yet another embodiment of the rotor provides that at least one backplane bus has a recess in which and through which the electrical connection elements are accessible for the electrical contacting with the electrical components. For example, this is not a continuous recess, and the electrical connection elements are advantageously arranged in the base and/or at the edges of the recess. The outer contour of the recess is designed to match the shape of at least one part of an electrical component of the rotor. For example, it is a continuous recess which is arranged and designed in a backplane bus such that it enables an access for contacting the electrical connection elements of an additional backplane bus.

In another embodiment of the rotor provides that the at least one backplane bus and the electrical components of the computed tomography apparatus are arranged on opposite sides of the rotatable mechanical support frame of the rotor. The mechanical attachment of the electrical components and their electrical wiring are therefore spatially separated so that the mechanical mounting of the components can be optimized, while the electrical connection of the components takes place via the at least one backplane bus. The at least one backplane bus is preferably attached to the rotatable mechanical support frame, preferably to one side of the rotatable support frame.

The backplane bus can be arranged at the rotatable mechanical support frame such that electrical components to be contacted are arranged in the region of the one side of the rotatable mechanical support frame while the backplane bus is arranged in the region of the other side.

In another embodiment of the rotor, the rotatable support frame has at least one continuous recess for at least one electrical component which is designed such that the electrical connection elements for the electrical contacting with the electrical components are accessible. The at least one continuous recess is preferably designed to accommodate an electrical component. The accommodation is preferably designed such that it involves a positive connection with at least one part of an electrical component if this is attached to the rotatable mechanical support frame. The attachment of the electrical component to the rotatable mechanical support frame is thereby simplified, and its attachment is improved, in particular in the rotating state. Moreover, it is thereby achieved that the attachment of the electrical component and its electrical contacting can occur independently of one another. For example, the rotating mechanical support frame has multiple continuous recesses in which different electrical components can be arranged and attached, wherein the side of the electrical components that faces toward the backplane bus is designed for electrical contacting with the electrical connection elements. The rotor preferably has a (preferably continuous) recess for each electrical component which is attached to the rotor. All electrical components can be mechanically attached to the rotatable mechanical frame and be electrically connected to at least one backplane bus with the same principle.

In another embodiment of the rotor the electrical connection elements are at least one plug socket and/or at least one plug for electrical connection with at least one of the components in the manner of a plug connection. The electrical connection elements have a plug socket arrangement and/or a plug arrangement for electrical connection with at least one of the components. A simple, stable contact is thereby enabled.

In another embodiment of the rotor, the at least one plug socket and/or the at least one plug and/or a plug socket arrangement and/or a plug arrangement is arranged on a backplane bus. The at least one plug socket and/or the at least one plug and/or a plug socket and/or a plug arrangement is preferably arranged in the floor of a recess in at least one backplane bus. The rotor preferably has at least two backplane buses, and the at least one plug socket and/or the at least one plug is arranged on a first backplane bus, wherein the other backplane bus has a continuous recess whereby the at least one plug socket and/or the at least one plug can be electrically connected with at least one of the components.

In another embodiment of the rotor, the electrical connection between the electrical components and the respective electrical connection elements of the at least one backplane bus takes place via a mechanical shorting of the respective electrical component with the rotor. It is thereby achieved that the electrical components are simultaneously electrically connected to the rotor upon their mechanical attachment and mounting on said rotor. The subsequent electrical connection is thereby omitted, so the installation of the components is significantly simplified.

In another embodiment of the rotor, at least one backplane bus has a slip ring, wherein the at least one slip ring is electrically connected with at least one electrical connection element of at least one backplane bus. The slip ring is preferably attached on one side of the at least one backplane bus which is facing away from the electrical components of the rotor. The power and/or signal transmission between the components of the rotor and the stationary part of the computed tomography apparatus can take place via the slip ring. The slip ring is preferably integrated into at least one backplane bus and forms a unit with this.

Furthermore, the invention concerns a rotating unit of a computed tomography apparatus with such a rotor.

The invention also concerns a computed tomography apparatus, preferably with a tiltable rotating unit, with such a rotor.

An exemplary embodiment of the invention is presented in the attached schematic drawings. In the figures, identical or functionally identical elements are provided throughout with the same reference characters. The depictions in the figures are schematic and not necessarily true to scale. In the following, and without limitation of generality, the device and the computed tomography apparatus are described only insofar as is necessary to understand the invention.

DESCRIPTION OF THE PREFERRED EMBODIMENTS

Figure 1:
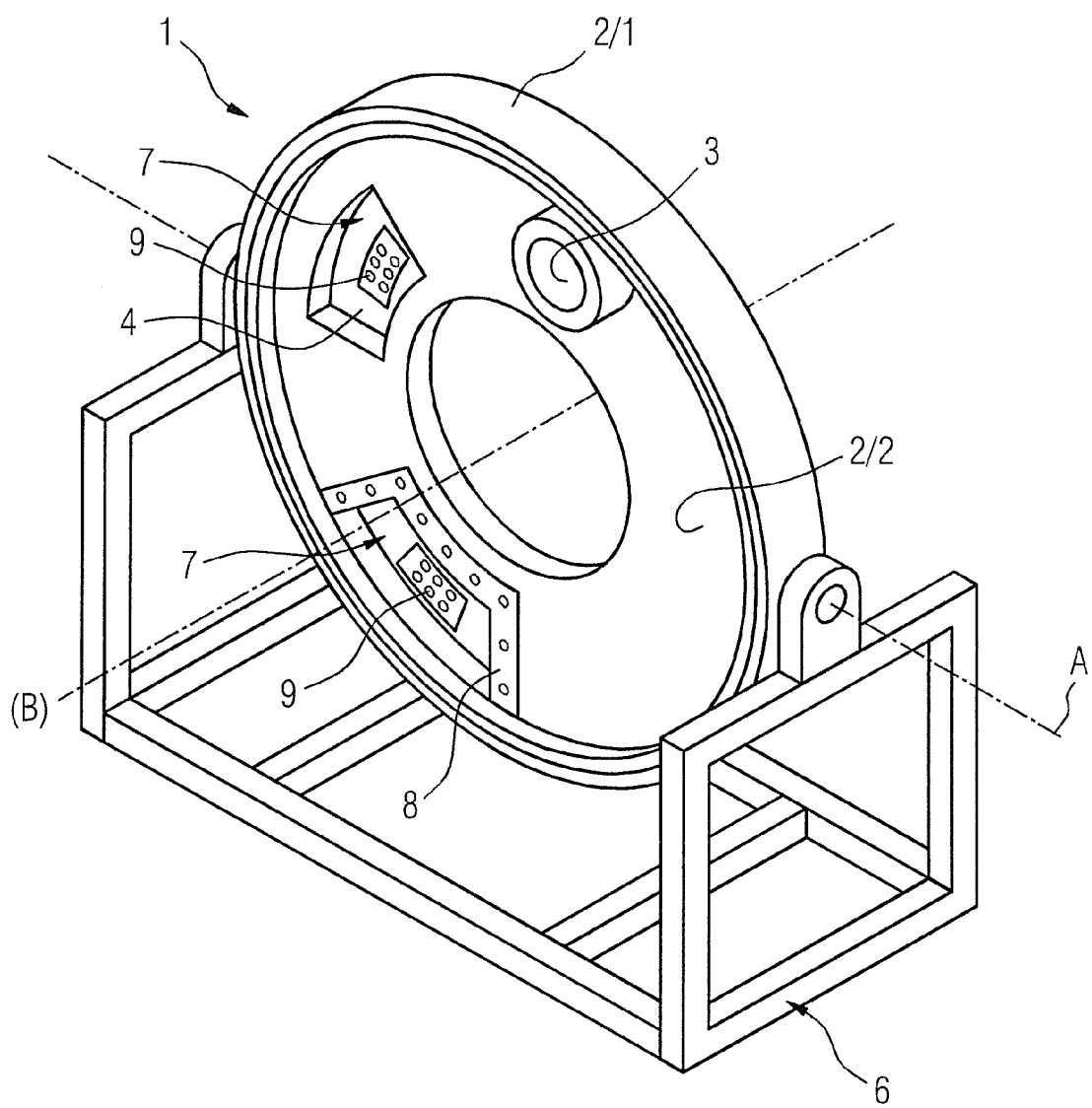
FIG. 1 is a schematic depiction of a tiltable rotor of a computed tomography apparatus with a stationary frame and a rotatable mechanical frame for mechanical mounting of electrical components, as well as a backplane bus mounted to the side of the rotatable mechanical frame.

FIG. 1 is a schematic depiction of a tiltable rotor 1 of a computed tomography apparatus with a stationary mechanical frame 2/1, the electrical component 3 over a bearing with a rotatable mechanical frame 2/2 as mechanical mount, and a backplane bus 4 attached laterally to the rotatable mechanical frame 2/2. The rotor 1 is supported or mounted so as to be tiltable on an axis A, relative to a stationary part 6. The rotatable mechanical frame 2/2 has various continuous recesses 7, which are designed for the accommodation of different electrical components 3. The rotatable mechanical frame 2/2 also has attachment surfaces 8 which, for example, are formed around the continuous recesses 7 for accommodation of the electrical component 3. The backplane bus 4 has electrical connection elements 5 for electrical contacting of the electrical component 3. In particular, the backplane bus 4 has electrical feed lines which are integrated into said backplane bus 4, as well as connectors 9—fashioned here as a plug socket arrangement or plug connector arrangement, for example—which are arranged to one side of the backplane bus 4 such that they are accessible—through the continuous openings 7—from a side of the rotatable mechanical support frame 2/2 that faces away from the backplane bus 4. In particular, the rotatable mechanical support frame 2/2 has differently shaped continuous openings that are designed for a partial positive accommodation of different electrical components 3. In the present example, a component 3 (an x-ray source, for example) is shown in the installed state.

Figure 2:
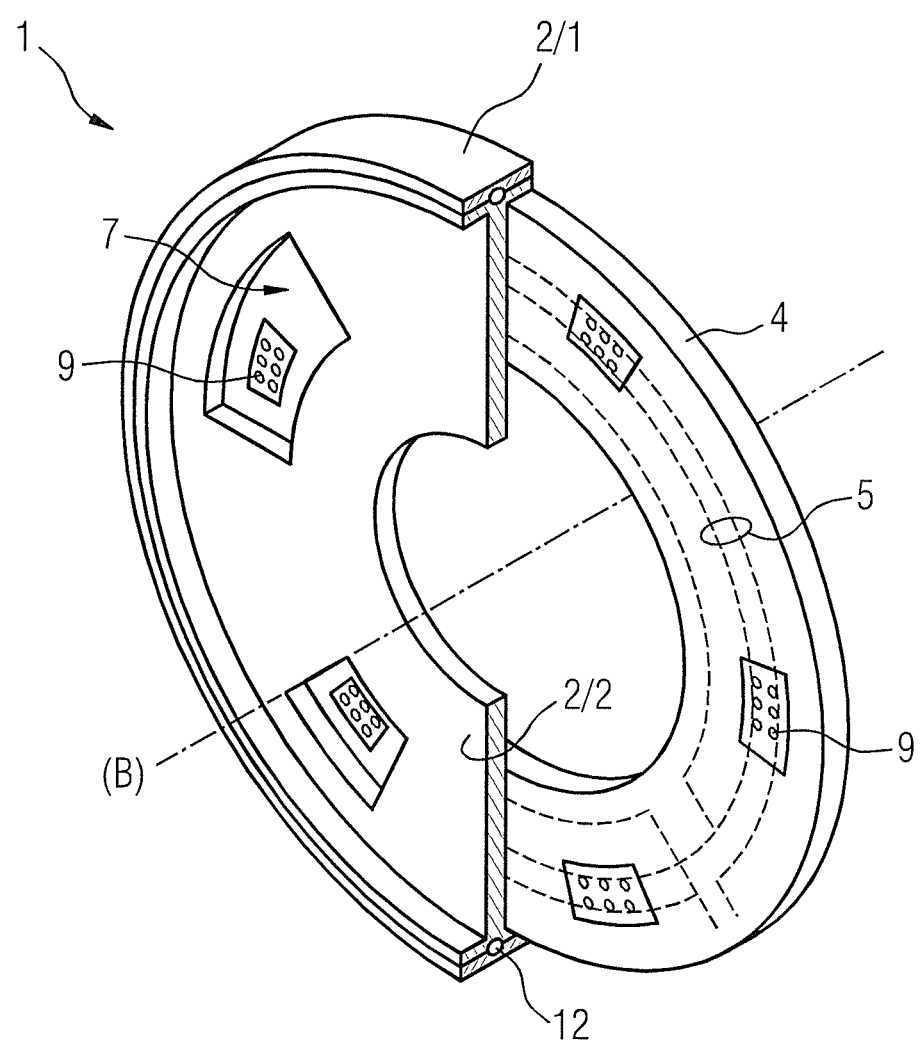
FIG. 2 is a schematic depiction of a rotor with a stationary frame and a rotatable mechanical frame for mechanical mounting of electrical components, as well as a backplane bus mounted to the side of the mechanical frame, which backplane bus has integrated electrical connection elements.

FIG. 2 shows a schematic partial depiction of a rotor 1 with a stationary frame 2/1 and a rotatable mechanical frame 2/2 for mechanical retention of electrical components 3, as well as a backplane bus 4 attached to the side of the rotatable mechanical frame 2/2, which backplane bus 4 has integrated electrical connection elements 5. The rotatable mechanical frame 2/2 has continuous openings 7 to accommodate electrical components 3 and a backplane bus 4 with multiple connectors 9 for electrical contacting of the electrical components 3, wherein the continuous openings 7 of the rotatable mechanical frame 2/2 and the connectors 9 of the electrical connection elements 5 are arranged such that—through the continuous openings 7—the connectors 9 of the electrical connection element are accessible from the side of the rotatable mechanical frame 2/2 that faces away from the backplane bus 4. In the present case, the stationary mechanical frame 2/1 and the rotatable mechanical frame 2/2 are drawn only in part in order to enable a view of the backplane bus 4. The backplane bus 4 is thereby laterally attached to the side of the rotatable mechanical frame 2/2. In the backplane bus 4, feed lines of the electrical connection elements 5 are depicted schematically (and only as an example) as dashed lines. In an example that is not shown, the rotor 1 has a second backplane bus which is connected with the first backplane bus 4, wherein electrical connection elements of different functions are fashioned in both backplane buses.

Figure 3:
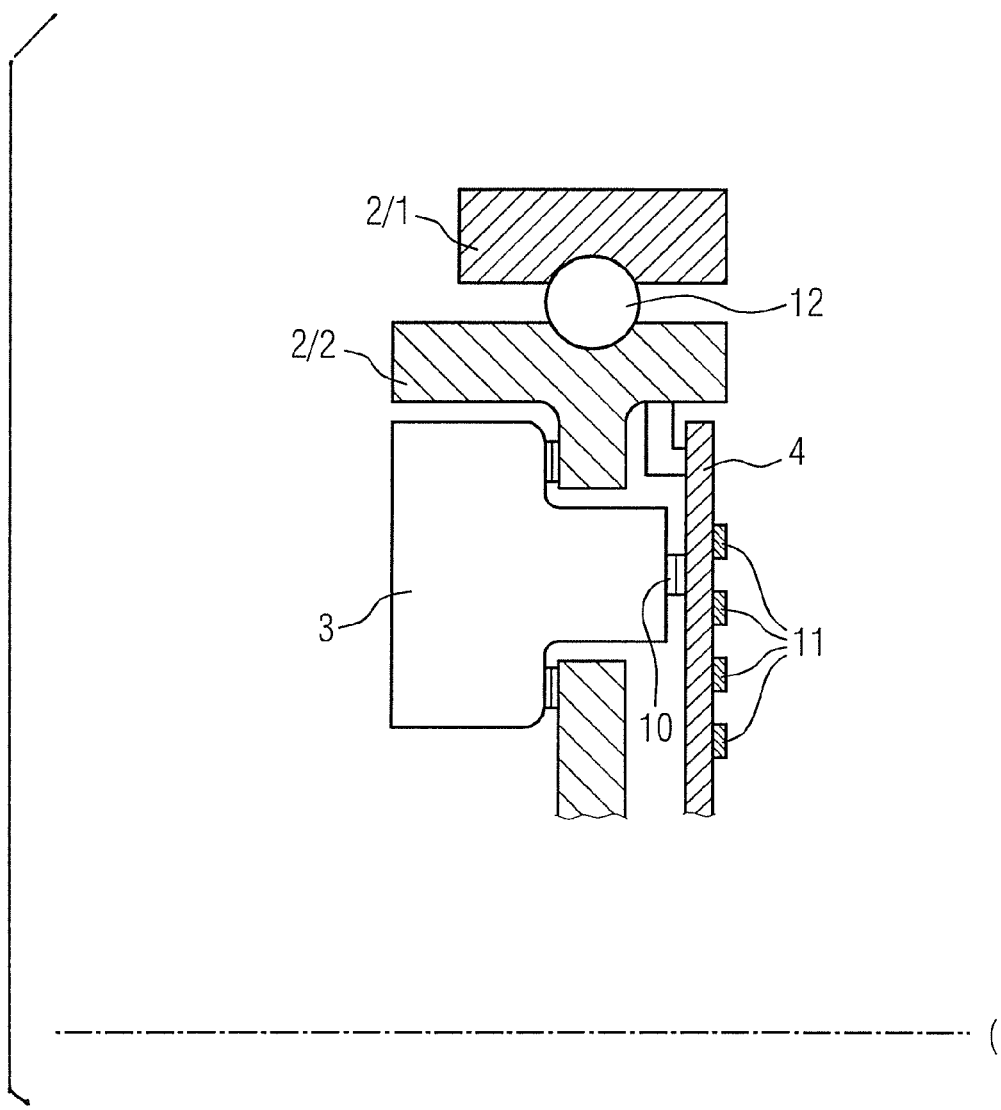
FIG. 3 shows a schematic partial section presentation of the rotor from FIG. 2, orthogonal to system axis B.

FIG. 3 shows as an example and, in a simplified form, a section presentation of the rotor 1 from FIG. 1, orthogonal to the system axis B of said rotor 1. Only the part of the section presentation that is located across the system axis B is thereby shown. A bearing 12 which allow the rotation of the rotatable mechanical support frame 2/2 relative to the stationary frame 2/1 is arranged between the stationary mechanical frame 2/1 and the rotatable mechanical support frame 2/2. Furthermore, a component 3 integrated into the rotatable support frame 2/2 is shown, the component 3 being connected (for example via a plug connection 10) with the electrical connection elements 5 of the backplane bus 4. Furthermore, the back side of the backplane bus 4 has four slip rings with slip ring traces 11 which, for example, can be electrically connected with oppositely arranged stationary brushes (not shown).

Although modifications and changes may be suggested by those skilled in the art, it is the intention of the inventors to embody within the patent warranted hereon all changes and

We claim as our invention:

1. A rotor of a computed tomography apparatus, comprising:
   a rotatable mechanical support frame that extends in a plane completely around a central opening therein, configured for rotatable mounting in an x-ray computed tomography apparatus so as to rotate, in said plane that includes said central opening, around a central axis that proceeds through said central opening, and configured to mechanically retain a plurality of x-ray computed tomography data-producing electrical components circumferentially distributed around said central opening; and
   at least one backplane bus mechanically attached to said support frame and having a central opening therein that is concentric with the central opening in the mechanical support frame, said at least one backplane bus also extending in a plane completely around the central opening therein, so as to be planarly adjacent to said mechanical support frame, said backplane bus comprising a plurality of electrical connection elements thereon configured to place said x-ray computed tomography data-producing electrical components in electrical communication with each other on said support frame.

2. A rotor as claimed in claim 1 wherein said electrical connection elements are configured for transmitting signals of a signal type selected from the group consisting of information-carrying signals and power signals.

3. A rotor as claimed in claim 1 comprising a first backplane bus and a second backplane bus, each having electrical connection elements thereon, with the electrical connection elements of said first backplane bus being configured for transmission of information-carrying signals, and the electrical connection elements on said second backplane bus being configured for power transmission.

4. A rotor as claimed in claim 1 wherein said at least one backplane bus comprises at least one of said x-ray computed tomography data-producing electrical components thereon that is accessible for making direct x-ray computed tomography data-producing electrical contact with at least one of said electrical components.

5. A rotor as claimed in claim 1 wherein said x-ray computed tomography data-producing electrical components are mounted on a first side of said support frame, and said backplane bus is attached to a second side of support frame opposite to said first side.

6. A rotor as claimed in claim 1 wherein said support frame comprises at least one continuous recess therein configured to receive at least one of said x-ray computed tomography data-producing electrical components, said recess being situated on said support frame to make said electrical connection elements accessible for making electrical contact with said at least one x-ray computed tomography data-producing electrical component in said recess.

7. A rotor as claimed in claim 6 comprising one recess in said support frame for each of said x-ray computed tomography data-producing electrical components.

8. A rotor as claimed in claim 1 wherein said electrical connection elements comprise at least one plug socket or at least one plug to make a plugged electrical connection with at least one of said x-ray computed tomography data-producing electrical components.

9. A rotor as claimed in claim 8 wherein said at least one plug socket or said at least one plug is attached at said at least one backplane bus.

10. A rotor as claimed in claim 1 wherein electrical connection between the x-ray computed tomography data-producing electrical components and the electrical connection elements comprises a mechanical shorting of the respective x-ray computed tomography data-producing electrical component with said support frame.

11. A rotor as claimed in claim 1 comprising at least one slip ring, said at least one slip ring being electrically connected with at least one of said electrical connection elements of said backplane bus.

12. A rotor as claimed in claim 11 wherein said slip ring and said at least one backplane bus form a unitary structure.

13. A rotating unit of an x-ray computed tomography apparatus, comprising:
   a plurality of x-ray computed tomography data-producing electrical components;
   a rotatable mechanical support frame that extends in a plane completely a central opening therein, configured for rotatable mounting in a computed tomography apparatus so as to rotate, in a plane that includes said central opening, around a central axis that proceeds through said central opening, and configured to mechanically retain said plurality of x-ray computed tomography data-producing electrical components circumferentially distributed around said central opening; and
   at least one backplane bus mechanically attached to said support frame and having a central opening therein that is concentric with the central opening in the mechanical support frame, said at least one backplane bus also extending in a plane completely around the central opening therein, so as to be planarly adjacent to said mechanical support frame, said backplane bus comprising a plurality of electrical connection elements thereon configured to place said x-ray computed tomography data-producing electrical components in electrical communication with each other on said support frame.

14. An x-ray computed tomography apparatus comprising:
   a stationary mount;
   a rotor that is rotatably mounted in said stationary mount;
   a plurality of x-ray computed tomography data-producing electrical components;
   said rotor comprising a rotatable mechanical support frame that extends in a plane completely a central opening therein rotatably mounted in said stationary mount so as to rotate, in a plane that includes said central opening, around a central axis that proceeds through said central opening, and configured to mechanically retain said plurality of x-ray computed tomography data-producing electrical components circumferentially distributed around said central opening; and
   at least one backplane bus mechanically attached to said support frame and having a central opening therein that is concentric with the central opening in the mechanical support frame, said at least one backplane bus also extending in a plane completely around the central opening therein, so as to be planarly adjacent to said mechanical support frame, said backplane bus comprising a plurality of electrical connection elements thereon configured to place said x-ray computed tomography data-producing electrical components in electrical communication with each other on said support frame.

15. A computed tomography apparatus as claimed in claim 14 wherein said rotor is also tiltably mounted in said stationary support so as to tilt around a tilting axis that is perpendicular to said central axis.

* * * * *